US010004861B2

(12) United States Patent
Wu et al.

(10) Patent No.: US 10,004,861 B2
(45) Date of Patent: Jun. 26, 2018

(54) ALARMING METHOD FOR VENTILATOR AND VENTILATOR ALARM SYSTEM

(71) Applicants: Landseed Hospital, Taoyuan County (TW); National Central University, Taoyuan (TW)

(72) Inventors: Chin-Pyng Wu, Taoyuan County (TW); Shih-Hsing Yang, Taoyuan County (TW); Kuo-Kai Shyu, Taoyuan County (TW); Chung-Chih Huang, Taoyuan County (TW); Chun-Ming Peng, Taoyuan County (TW); Yuh-Chin Huang, Taoyuan County (TW)

(73) Assignees: Landseed Hospital, Taoyuan County (TW); National Central University, Taoyuan (TW)

( * ) Notice: Subject to any disclaimer, the term of this patent is extended or adjusted under 35 U.S.C. 154(b) by 697 days.

(21) Appl. No.: 14/698,853

(22) Filed: Apr. 29, 2015

(65) Prior Publication Data
US 2015/0314090 A1 Nov. 5, 2015

(30) Foreign Application Priority Data
Apr. 30, 2014 (TW) .............................. 103115572 A

(51) Int. Cl.
*A61M 16/00* (2006.01)
*G01L 19/12* (2006.01)

(52) U.S. Cl.
CPC .... *A61M 16/0051* (2013.01); *A61M 16/0003* (2014.02); *A61M 16/0069* (2014.02);
(Continued)

(58) Field of Classification Search
CPC ........... A61M 16/0051; A61M 16/021–16/026
See application file for complete search history.

(56) References Cited

U.S. PATENT DOCUMENTS

| 2005/0092324 | A1* | 5/2005 | Bowden | A61H 31/005 128/204.21 |
| 2006/0037615 | A1* | 2/2006 | Wilkinson | A61B 5/08 128/204.23 |
| 2011/0313689 | A1* | 12/2011 | Holley | A61B 5/087 702/56 |

OTHER PUBLICATIONS

Shih-Hsing Yang et al., "Intelligent Alarm System of Mechanical Ventilation: Innovative Pressure Alarm for Immediate Clinical Management ", Biomedical Engineering and Biotechnology (iCBEB), 2012 International Conference on, May 2012, 336-339.
(Continued)

*Primary Examiner* — Valerie L Woodward
(74) *Attorney, Agent, or Firm* — JCIPRNET

(57) ABSTRACT

An alarming method for a ventilator and a ventilator alarm system are provided. The method includes the following. First, a plurality of ventilation parameters are received and detected. If a peak airway pressure of the ventilation parameters conforms to a first condition, whether a plateau pressure conforms to a second condition is determined, wherein the first condition is $Y_{(k+1), Ppeak} > Y_{k, mean,Ppeak} + 3 * Y_{k,sd,Ppeak}$, and the second condition is $Y_{(k+1), Pplateau} < Y_{k, mean, Pplateau} + 3 * Y_{k, sd, Pplateau}$. If the plateau pressure does not conform to the second condition, an airway static obstruction alarm is activated. If the plateau pressure conforms to the second condition and a third condition, an airway dynamic obstruction alarm is activated.

22 Claims, 13 Drawing Sheets

(52) U.S. Cl.
CPC ........... *A61M 16/021* (2017.08); *G01L 19/12* (2013.01); *A61M 16/0006* (2014.02); *A61M 2016/003* (2013.01); *A61M 2016/0027* (2013.01); *A61M 2016/0039* (2013.01); *A61M 2016/0042* (2013.01); *A61M 2205/18* (2013.01); *A61M 2205/3334* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2230/46* (2013.01)

(56) References Cited

OTHER PUBLICATIONS

"Office Action of Taiwan Counterpart Application", dated May 6, 2016, p. 1-p. 6, in which the listed reference was cited.

* cited by examiner

ALARMING METHOD FOR VENTILATOR AND VENTILATOR ALARM SYSTEM

CROSS-REFERENCE TO RELATED APPLICATION

This application claims the priority benefit of Taiwan application serial no. 103115572, filed on Apr. 30, 2014. The entirety of the above-mentioned patent application is hereby incorporated by reference herein and made a part of this specification.

BACKGROUND OF THE INVENTION

Field of the Invention

The invention relates to an alarm system and particularly relates to an alarming method for a ventilator and a ventilator alarm system.

Description of Related Art

A ventilator is a mechanical device used in place of a pump function of a human respiratory organ, mainly for ventilation and oxygenation of a patient who has respiratory failure and for reducing work of breathing, so as to maintain appropriate carbon dioxide and oxygen content in the blood for the patient to breathe easily. While providing the patient a respiratory treatment, the current ventilator also detects and displays various parameters of the patient's respiratory status (referred to as "ventilation parameters" hereinafter). Thus, when the patient has a breathing problem, the problem can be shown by the ventilation parameters for the medical staff to react immediately.

The breathing problem is usually very urgent and may very likely cause great harm to the patient if the problem is not dealt with properly within minutes. However, due to the limited number of the medical staff, it is impossible for the medical staff to observe each patient's ventilation parameters all day. In addition, when abnormal ventilation parameters occur, simply adjusting the operational setting of the ventilator is usually not enough, and from time to time the medical staff are required to provide first aid or various treatments according to the conditions. Although the current ventilator may be connected to an alarm system for notifying the medical staff, the poor design of the alarm signals of the current alarm system only provides single-parameter alarms and often activates false positive alarms, and thus cannot convey clear information for the medical staff to make decisions immediately. For example, in an ICU alarm investigation, the proportion of incorrect and false positive alarms is extremely high. Among 1455 alarms, only 8 correctly show the potential threats to the patients' lives.

In view of the above, how to establish an accurate and efficient alarm system has become an important issue in this field of medical care.

SUMMARY OF THE INVENTION

The invention provides an intelligent alarming method for a ventilator and an intelligent ventilator alarm system, which provide effective alarm and immediate operational management for the medical staff through alarm signals activated by a variety of abnormal respiratory data, which may include patient data collection management and alarms of conditions of suctioning, loose pipe, or air leak.

The invention provides an alarming method for a ventilator, and the alarming method includes the following. First, a plurality of ventilation parameters are received and detected. If a peak airway pressure of the ventilation parameters conforms to a first condition, whether a plateau pressure conforms to a second condition is determined, wherein the first condition is $Y_{(k+1), Ppeak} > Y_{k, mean, Ppeak} + 3*Y_{k,sd,Ppeak}$ and the second condition is $Y_{(k+1), Pplateau} < Y_{k, mean, Pplateau} + 3*Y_{k, sd, Pplateau}$, wherein k is a positive integer which indicates a $k^{th}$ sample, $Y_{(k+1), Ppeak}$ indicates the peak airway pressure of a $k+1^{th}$ sample, $Y_{k, mean, Ppeak}$ and $Y_{k,sd,Ppeak}$ respectively indicate a moving average and a standard deviation of the peak airway pressure obtained based on the $k^{th}$ sample, $Y_{(k+1), Pplateau}$ indicates the plateau pressure of the $k+1^{th}$ sample, and $Y_{k, mean, Pplateau}$ and $Y_{k, sd, Pplateau}$ respectively indicate a moving average and a standard deviation of the plateau pressure based on the $k^{th}$ sample. If the plateau pressure does not conform to the second condition, an airway static obstruction alarm is activated. If the plateau pressure conforms to the second condition and an expiratory flow of the ventilation parameters conforms to a third condition, an airway dynamic obstruction alarm is activated.

The invention further provides a ventilator alarm system, which includes a ventilator, a control unit, and a monitoring apparatus. The ventilator is configured to receive a plurality of ventilation parameters of a patient. The control unit receives the ventilation parameters from the ventilator, detects the ventilation parameters, and determines whether the ventilation parameters conform to a plurality of conditions. The monitoring apparatus is configured to display information corresponding to the ventilation parameters and issue a plurality of alarms. If the control unit determines that a peak airway pressure of the ventilation parameters conforms to a first condition, the control unit further determines whether a plateau pressure conforms to a second condition, wherein the first condition is $Y_{(k+1), Ppeak} > Y_{k, mean, Ppeak} + 3*Y_{k,sd,Ppeak}$ and the second condition is $Y_{(k+1), Pplateau} < Y_{k, mean, Pplateau} + 3*Y_{k, sd, Pplateau}$, wherein k is a positive integer which indicates a $k^{th}$ sample, $Y_{(k+1), Ppeak}$ indicates the peak airway pressure of a $k+1^{th}$ sample, $Y_{k, mean, Ppeak}$ and $Y_{k,sd,Ppeak}$ respectively indicate a moving average and a standard deviation of the peak airway pressure obtained based on the $k^{th}$ sample, $Y_{(k+1), Pplateau}$ indicates the plateau pressure of the $k+1^{th}$ sample, and $Y_{k, mean, Pplateau}$ and $Y_{k, sd, Pplateau}$ respectively indicate a moving average and a standard deviation of the plateau pressure based on the $k^{th}$ sample. If the control unit determines that the plateau pressure does not conform to the second condition, the monitoring apparatus activates the airway static obstruction alarm. If the control unit determines that the plateau pressure conforms to the second condition and an expiratory flow of the ventilation parameters conforms to a third condition, the monitoring apparatus activates an airway dynamic obstruction alarm.

Based on the above, the alarming method for the ventilator and the ventilator alarm system of the embodiments of the invention are configured to retrieve specific ventilation parameters, e.g. peak airway pressure, plateau pressure, and expiratory flow, to determine whether the ventilation parameters conform to one or multiple conditions. When the ventilation parameters conform to the conditions, the corresponding alarm, e.g. airway static obstruction alarm, airway dynamic obstruction alarm, loose pipe alarm, or air leak alarm, is activated instantly. Accordingly, the medical staff can react immediately according to the accurate alarms to improve the patient's safety.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
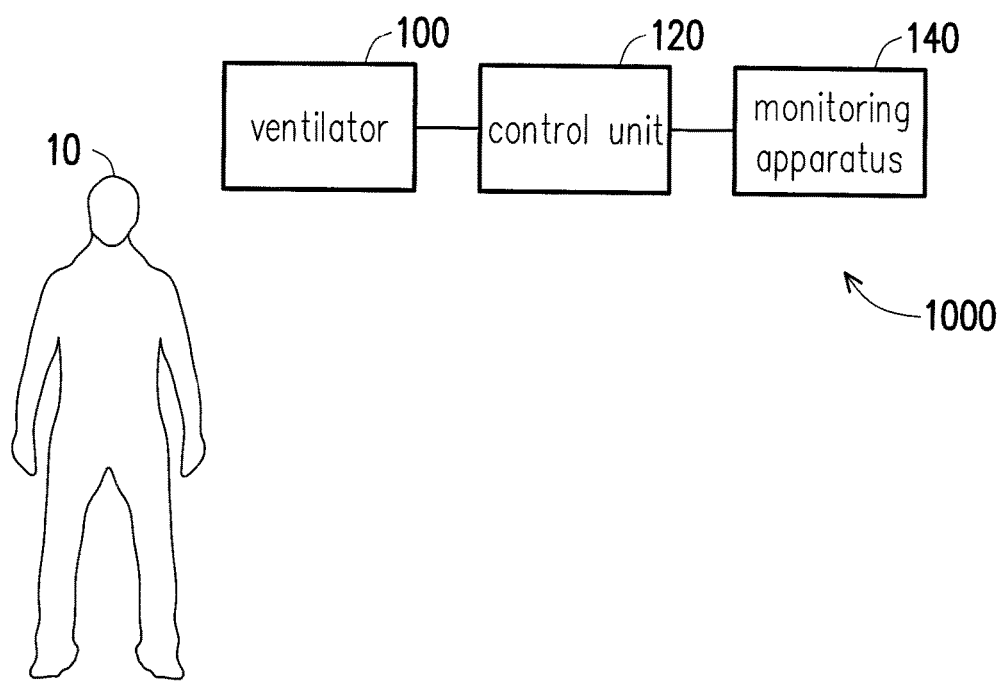
FIG. 1 is a block diagram illustrating a ventilator alarm system according to an embodiment of the invention.

FIG. 1 is a block diagram illustrating a ventilator alarm system according to an embodiment of the invention. With reference to FIG. 1, a ventilator alarm system 1000 of this embodiment includes a ventilator 100, a control unit 120, and a monitoring apparatus 140, wherein the ventilator 100 is configured to receive a plurality of ventilation parameters of a patient 10, and the control unit 120 is configured to determine whether the ventilation parameters conform to one or a plurality of conditions. If the ventilation parameter conforms to the condition, the monitoring apparatus 140 activates an alarm immediately to notify the medical staff instantly. Functions of the ventilator 100, the control unit 120, and the monitoring apparatus 140 are described in detail below.

The ventilator 100 is configured to provide oxygen to the patient. More specifically, the ventilator 100 may be connected to a respiratory organ of the patient for ventilation of the patient through a pipe, and the ventilator 100 simultaneously provides read-time information (e.g. flow, resistance, pressure, and so on) about a breathing condition of the patient, which is the ventilation parameter. In addition, the ventilator 100 may be connected to a flow sensor for detecting the ventilation parameter of gas in a hose.

The control unit 120 regularly receives and detects an operating condition of the ventilator 100. In this embodiment, the control unit 120 is connected to the ventilator 100 through a connector having an Rs232 communication interface, for example, so as to access the ventilation parameters. More specifically, for example, the control unit 120 receives the ventilation parameters of a positive end expiratory pressure (PEEP), an expiratory tidal volume (Exp.Volume), an inspiratory tidal volume (Insp.Volume), a peak airway pressure (Ppeak), a minute ventilation (MV), a plateau pressure (Pplateau), a percentage of inhaled oxygen, a respiratory rate, an airway resistance (Rexp), an expiratory flow (Fexp), and expiratory flow waveform information thereof from the ventilator 100 at a preset time interval (e.g. 0.5 second). In addition, the control unit 120 may convert the ventilation parameters to digital transmission data, compatible with the transmission control protocol/Internet protocol (TCP/IP), to be transmitted to the monitoring apparatus 140 through a wireless network or a wired network.

The monitoring apparatus 140 is configured to provide a human-computer interaction (HCI). The monitoring apparatus 140 is an electronic device having a processor, such as personal computer, laptop computer, tablet computer, mobile phone, smart phone, personal digital assistant (PDA), etc. However, it is noted that the invention is not limited thereto. More specifically, the monitoring apparatus 140 may include a screen and an alarm device, wherein the screen is configured to display a physiological message corresponding to the ventilation parameter, and the alarm device is configured to issue an alarm immediately when an abnormal ventilation parameter occurs. For example, the alarm device may issue an alarm through broadcasting, send an alarm message to a telephone device, or transmit an alarm message to a computer device and/or a handheld device of the medical staff through voice, E-mail, text message, or messages of other forms, so as to notify the medical staff instantly.

Figure 2A:
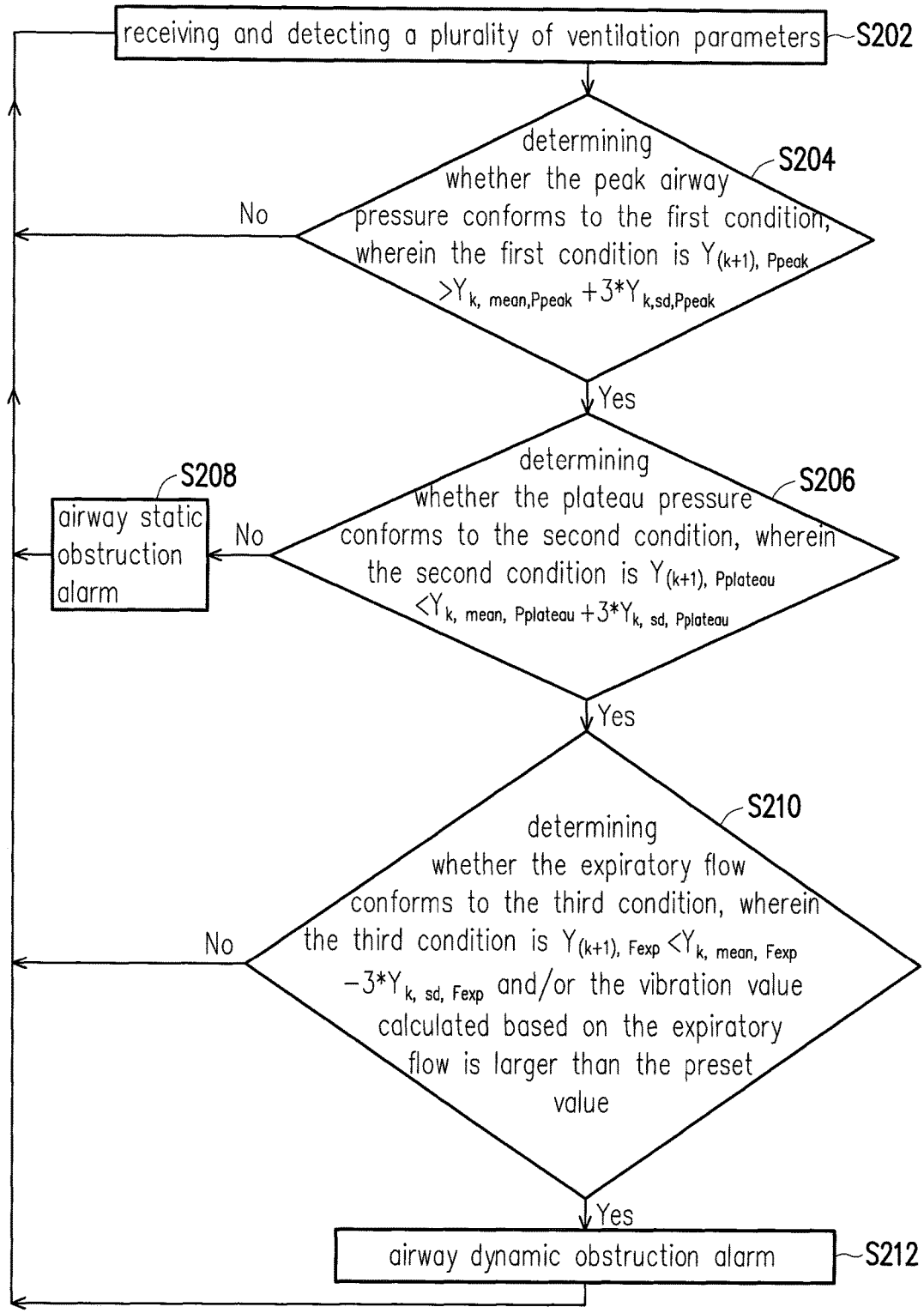
FIG. 2A is a flowchart illustrating an alarming method for a ventilator according to an embodiment of the invention.

The following introduces detailed steps of a ventilator alarming method of the embodiment with reference to the components in the ventilator alarm system 1000. FIG. 2A is a flowchart illustrating an alarming method for a ventilator according to an embodiment of the invention. With reference to FIG. 2A, in Step S202, the ventilator 100 is used to receive a plurality of ventilation parameters of the patient 10, wherein the ventilation parameters include the positive end expiratory pressure (PEEP), the expiratory tidal volume (Exp.Volume), the inspiratory tidal volume (Insp.Volume), the peak airway pressure (Ppeak), the minute ventilation (MV), the plateau pressure (Pplateau), the airway resistance (Rexp), the expiratory flow (Fexp), the percentage of inhaled oxygen, and the respiratory rate, for example. Moreover, the control unit 120 receives the ventilation parameters from the ventilator 100 and detects the ventilation parameters obtained from the ventilator 100, thereby determining whether the ventilation parameters conform to one or a plurality of conditions in the subsequent steps, for determining whether the patient 10 has an abnormal physiological condition based on the ventilation parameters. Here, based on five ventilation parameters consecutively obtained by the ventilator 100, the control unit 120 calculates moving averages and standard deviations of the ventilation parameters in the five consecutive samples. Certainly, in other embodiments, the control unit 120 may also calculate the moving average and the standard deviation of each ventilation parameter based on other numbers of sample data (i.e. ventilation parameters).

In Step S204, the control unit 120 determines whether the peak airway pressure of the ventilation parameters conforms to a first condition, and the first condition is $Y_{(k+1), Ppeak} > Y_{k, mean, Ppeak} + 3*Y_{k, sd, Ppeak}$, wherein k is a positive integer which indicates the peak airway pressure Ppeak of a $k^{th}$ sample, $Y_{(k+1),\ Ppeak}$ indicates the peak airway pressure of a $k+1^{th}$ sample, and $Y_{k,\ mean,Ppeak}$ and $Y_{k,sd,Ppeak}$ respectively indicate the moving average and the standard deviation of the peak airway pressure obtained based on the $k^{th}$ sample.

If the peak airway pressure does not conform to the first condition, which means that the peak airway pressure is determined as a normal value, the control unit 120 does not activate an alarm, and as shown in Step S202, the control unit 120 continues to detect the next ventilation parameter obtained by the ventilator 100 to determine whether the next ventilation parameter is abnormal.

If the peak airway pressure conforms to the first condition, which means that the peak airway pressure is determined as abnormal, then as shown in Step S206, the control unit 120 further determines whether the plateau pressure Pplateau of the ventilation parameters conforms to a second condition, and the second condition is $Y_{(k+1),\ Pplateau} < Y_{k,\ mean,\ Pplateau} + 3*Y_{k,\ sd,\ Pplateau}$, wherein $Y_{(k+1),\ Pplateau}$ indicates the plateau pressure Pplateau of the $k+1^{th}$ sample, and $Y_{k,\ mean,\ Pplateau}$ and $Y_{k,\ sd,\ Pplateau}$ respectively indicate the moving average and the standard deviation of the plateau pressure Pplateau obtained based on the $k^{th}$ sample. Moreover, because the peak airway pressure conforms to the first condition, it indicates that the pressure in the airway exceeds a normal value (i.e. in a high-pressure state), and thus the control unit 120 may also activate a high-pressure alarm through the monitoring apparatus 140.

If the plateau pressure Pplateau does not conform to the second condition, then as shown in Step S208, the control unit 120 activates an airway static obstruction alarm through the monitoring apparatus 140. Generally, if the peak airway pressure Ppeak conforms to the first condition (i.e. the peak airway pressure Ppeak gradually increases) while the plateau pressure Pplateau does not conform to the second condition (i.e. the plateau pressure Pplateau increases gradually as well), it indicates that the patient has asthma. Accordingly, in this embodiment, the medical staff is notified of this situation immediately by the airway static obstruction alarm.

If the plateau pressure Pplateau conforms to the second condition, then as shown in Step S210, the control unit 120 further determines whether the expiratory flow of the ventilation parameters conforms to a third condition. In this embodiment, the third condition is $Y_{(k+1),\ Fexp} < Y_{k,\ mean,\ Fexp} - 3*Y_{k,\ sd,\ Fexp}$, wherein $Y_{(k+1),\ Pplateau}$ indicates the expiratory flow Fexp of the $k+1^{th}$ sample, and $Y_{k,\ mean,\ Pplateau}$ and $Y_{k,\ sd,\ Pplateau}$ respectively indicate the moving average and the standard deviation of the expiratory flow Fexp obtained based on the $k^{th}$ sample.

It is noted that, in another embodiment, the third condition may be determined based on the expiratory flow Fexp waveform information. That is, the third condition may be that a vibration value (Vib) calculated based on the expiratory flow Fexp is larger than a preset value. Specifically, a step of calculating the vibration value Vib includes performing a segmentation calculation on the expiratory flow Fexp and performing a curve fitting calculation to obtain a flow trend of the expiratory flow Fexp, and calculating a difference equation, based on a result of performing the segmentation calculation on the expiratory flow Fexp and the flow trend, and using the difference equation to calculate the vibration value Vib.

Figure 2B:
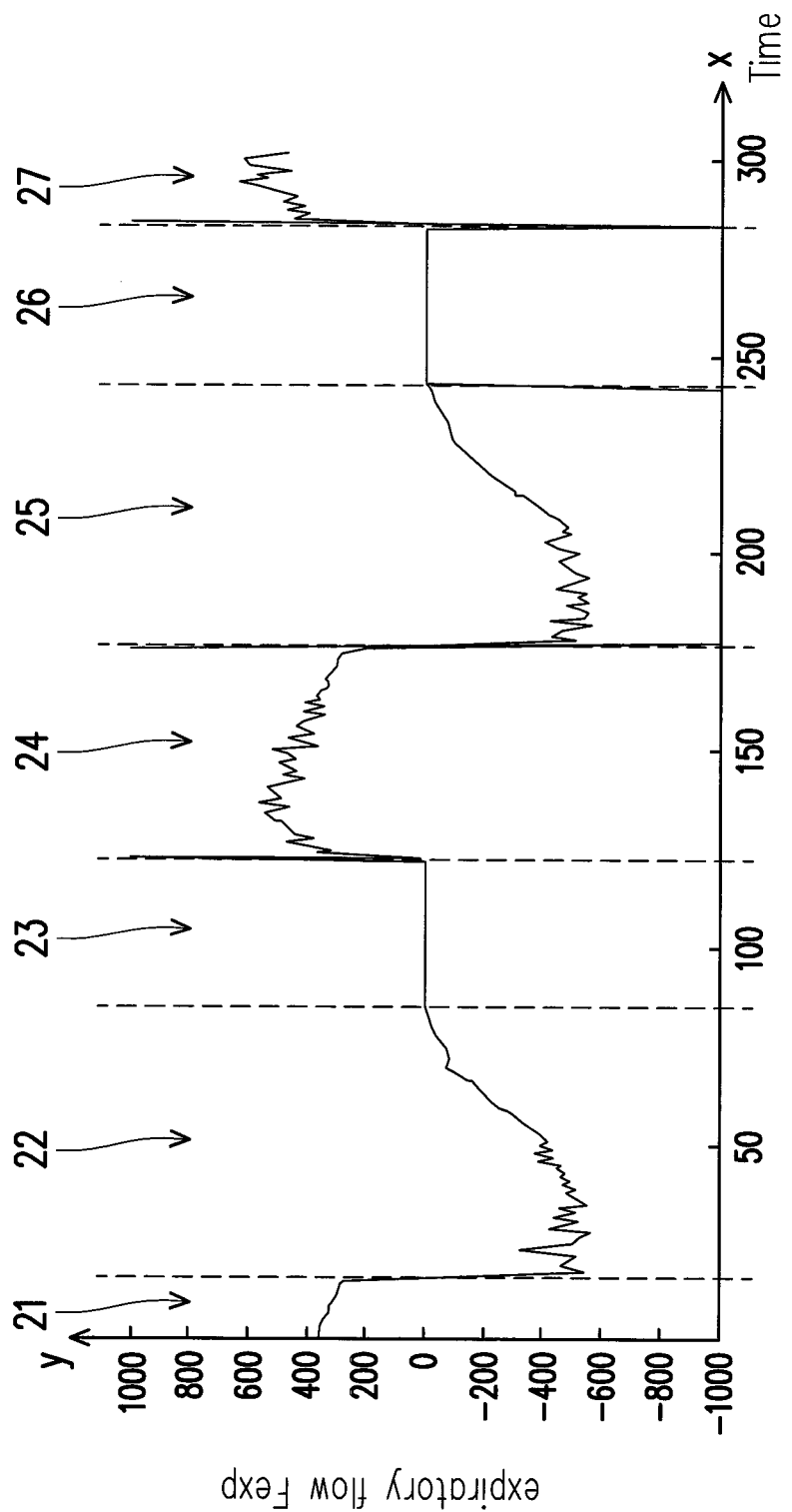
FIG. 2B to FIG. 2E are graphs illustrating calculation of vibration values.

FIG. 2B to FIG. 2E are graphs illustrating calculation of the vibration value, wherein a horizontal axis indicates time and a vertical axis indicates the expiratory flow Fexp. First, the control unit 120 segments a required segment according to the value of the expiratory flow Fexp. Here, the required segment is a segment where the value of the expiratory flow Fexp is larger than 0 or smaller than 0 and is a complete segment. As shown in FIG. 2B, the segments obtained by the control unit 120 are areas 22, 24, and 25. Because the values of the expiratory flow Fexp of areas 23 and 26 are 0 and the segments of areas 21 and 27 are incomplete, the segments of areas 21, 23, 26, and 27 are not obtained.

Figure 2C:
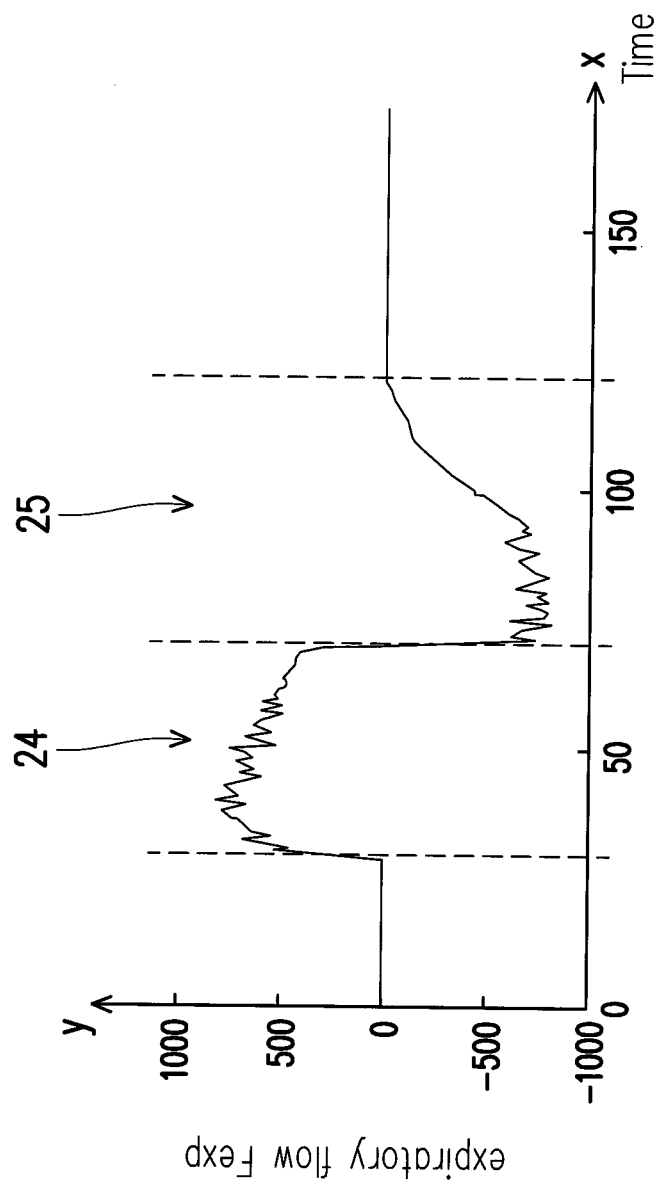
Figure 2D:
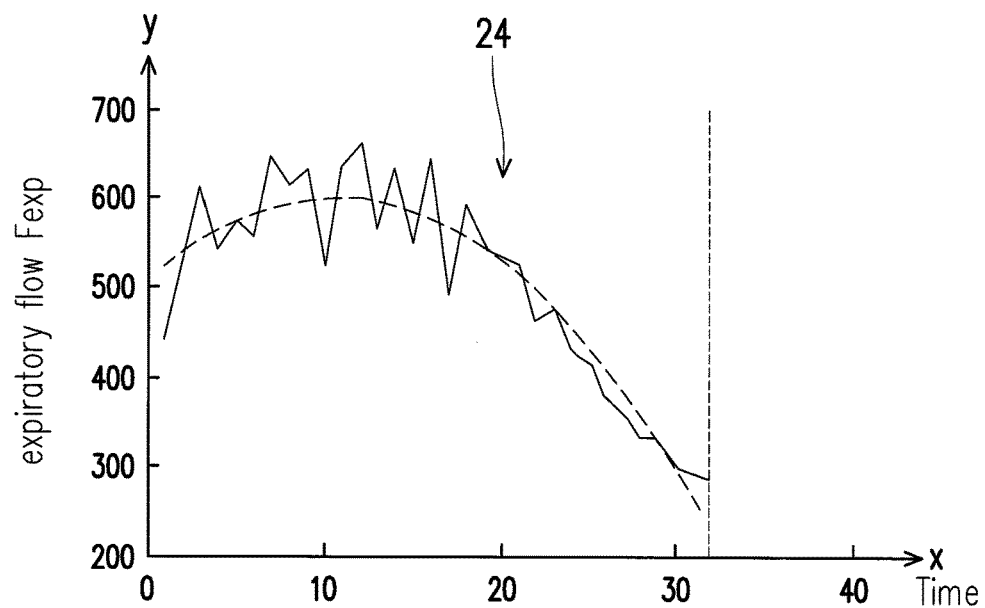
Figure 2E:
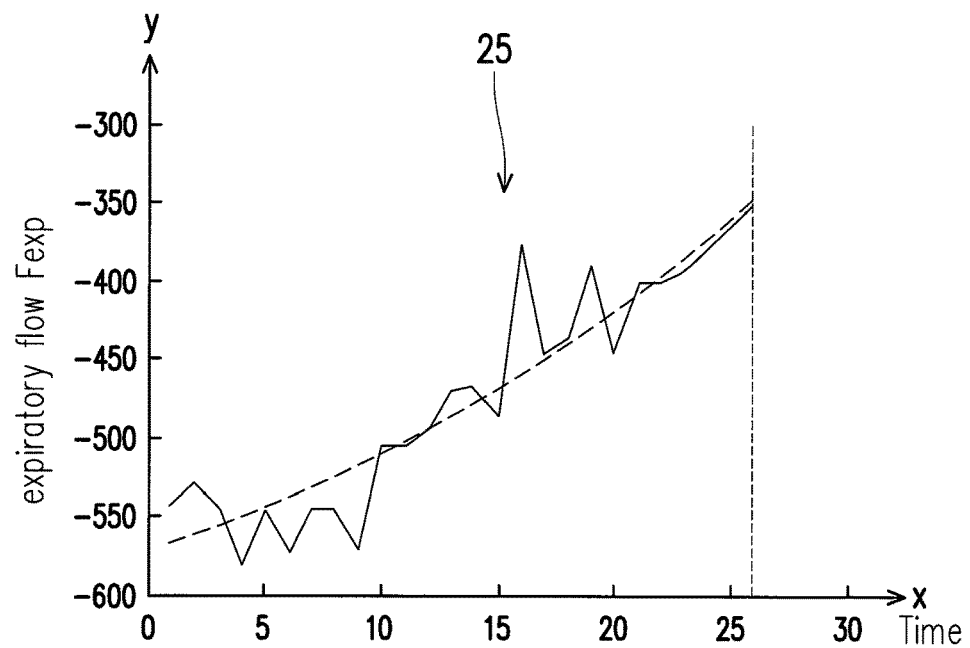

When the patient has sputum, the expiratory flow Fexp shows a saw-tooth waveform. In order to obtain the saw-tooth part, the curve fitting calculation is used first to calculate the trend of the expiratory flow Fexp. Take areas 24 and 25 as an example (as shown in FIG. 2C), the control unit 120 uses the expiratory flow Fexp values of areas 24 and 25 to perform the curve fitting calculation so as to obtain the trend of the expiratory flow Fexp, i.e. the smooth curves illustrated in FIG. 2D and FIG. 2E. An equation to be obtained by the curve fitting calculation may be represented by Equation (1) $\hat{Y} = \alpha + \beta X + \gamma X^2$, wherein $\alpha$, $\beta$, $\gamma$, and $\Delta$ are respectively defined as follows, and the length of X is determined by the number of segments after segmenting the expiratory flow Fexp.

$$\alpha = \frac{\begin{vmatrix} \sum_{i=1}^{n} y_i & \sum_{i=1}^{n} x_i & \sum_{i=1}^{n} x_i^2 \\ \sum_{i=1}^{n} x_i y_i & \sum_{i=1}^{n} x_i^2 & \sum_{i=1}^{n} x_i^3 \\ \sum_{i=1}^{n} x_i^2 y_i & \sum_{i=1}^{n} x_i^3 & \sum_{i=1}^{n} x_i^4 \end{vmatrix}}{\Delta},$$

$$\beta = \frac{\begin{vmatrix} n & \sum_{i=1}^{n} y_i & \sum_{i=1}^{n} x_i^2 \\ \sum_{i=1}^{n} x_i & \sum_{i=1}^{n} x_i y_i & \sum_{i=1}^{n} x_i^3 \\ \sum_{i=1}^{n} x_i^2 & \sum_{i=1}^{n} x_i^2 y_i & \sum_{i=1}^{n} x_i^4 \end{vmatrix}}{\Delta},$$

$$\gamma = \frac{\begin{vmatrix} n & \sum_{i=1}^{n} x_i & \sum_{i=1}^{n} y_i \\ \sum_{i=1}^{n} x_i & \sum_{i=1}^{n} x_i^2 & \sum_{i=1}^{n} x_i y_i \\ \sum_{i=1}^{n} x_i^2 & \sum_{i=1}^{n} x_i^3 & \sum_{i=1}^{n} x_i^2 y_i \end{vmatrix}}{\Delta},$$

$$\Delta = \begin{vmatrix} n & \sum_{i=1}^{n} x_i & \sum_{i=1}^{n} x_i^2 \\ \sum_{i=1}^{n} x_i & \sum_{i=1}^{n} x_i^2 & \sum_{i=1}^{n} x_i^3 \\ \sum_{i=1}^{n} x_i^2 & \sum_{i=1}^{n} x_i^3 & \sum_{i=1}^{n} x_i^4 \end{vmatrix}$$

In addition, the control unit 120 subtracts a value of the trend of the expiratory flow Fexp from a result obtained by segmentation calculation of the expiratory flow Fexp, so as to calculate a difference equation. Equation (2) of the difference equation is as follows:

$$D(X)=|\text{flow segmented}^1 \hat{Y}|, b1 \leq X \leq c1 \ \& \ a2 \leq X \leq b2 \ \& \quad \text{Equation (2),}$$

wherein the length of X is determined by the number of segments after the segmentation.

At last, the control unit 120 calculates the vibration value Vib by the difference equation (i.e. Equation (2)), wherein Equation (3) for calculating the vibration value Vib is as follows (based on three segments, for example):

$$Vib = \left( \frac{\sum_{i=b1}^{c1} d1_i + \sum_{i=a2}^{b2} d2_i}{(c1-b1+1)+(b2-a2+1)} + \frac{\sum_{i=a2}^{b2} d2_i + \sum_{i=b2}^{c2} d3_i}{(b2-a2+1)+(c2-b2+1)} \right) / 2, \quad \text{Equation (3)}$$

wherein d1 is $D(X), b1 \leq X \leq c1$, d2 is $D(X), a2 \leq X \leq b2$ and d3 is $D(X), b2 \leq X \leq c2$, and the value obtained by Equation (3) is the vibration value. In other words, when the vibration value Vib is larger than the preset value (may be set according to the requirement of measurement), i.e. the expiratory flow Fexp conforms to the third condition, it indicates that the patient has sputum. On the other hand, when the vibration value Vib is smaller than the preset value, i.e. the expiratory flow Fexp does not conform to the third condition, it indicates that the patient has no sputum.

Accordingly, if the expiratory flow Fexp does not conform to the third condition, as shown in Step S202, the control unit 120 continues to detect the next ventilation parameter obtained by the ventilator 100 to determine whether the next ventilation parameter is abnormal.

By contrast, if the expiratory flow Fexp conforms to at least one of the third condition, as shown in Step S212, the control unit 120 activates an airway dynamic obstruction alarm through the monitoring apparatus 140. Generally, if the peak airway pressure Ppeak conforms to the first condition (i.e. the peak airway pressure Ppeak gradually increases), the plateau pressure Pplateau conforms to the second condition (i.e. the plateau pressure Pplateau does not increase gradually or remains substantially unchanged), and the expiratory flow Fexp conforms to the third condition (i.e. the expiratory flow Fexp decreases gradually), it indicates that the patient has sputum. Accordingly, the control unit 120 may also activate a suctioning alarm and notify the medical staff of this situation immediately by the airway dynamic obstruction alarm.

Thus, in the ventilator alarm system 1000 of this embodiment, the control unit 120 determines whether the ventilation parameters obtained by the ventilator 100 conform to one or a plurality of conditions, thereby determining whether the patient 10 has an abnormal physiological condition. When an abnormal physiological condition occurs, e.g. sputum or asthma, because the ventilation parameter of the patient exceeds the normal value range, the control unit 120 issues the corresponding alarm based on the result of determination through the monitoring apparatus 140 to notify the medical staff immediately.

It should be noted that the ventilator alarm system 1000 of this embodiment may include other conditions, besides the first to the third conditions, for determining whether the ventilation parameters conform to the other conditions, so as to determine whether the breathing condition of the patient is abnormal and whether to activate an alarm. Another embodiment is given below with reference to the above-described ventilator alarm system 1000.

Figure 3:
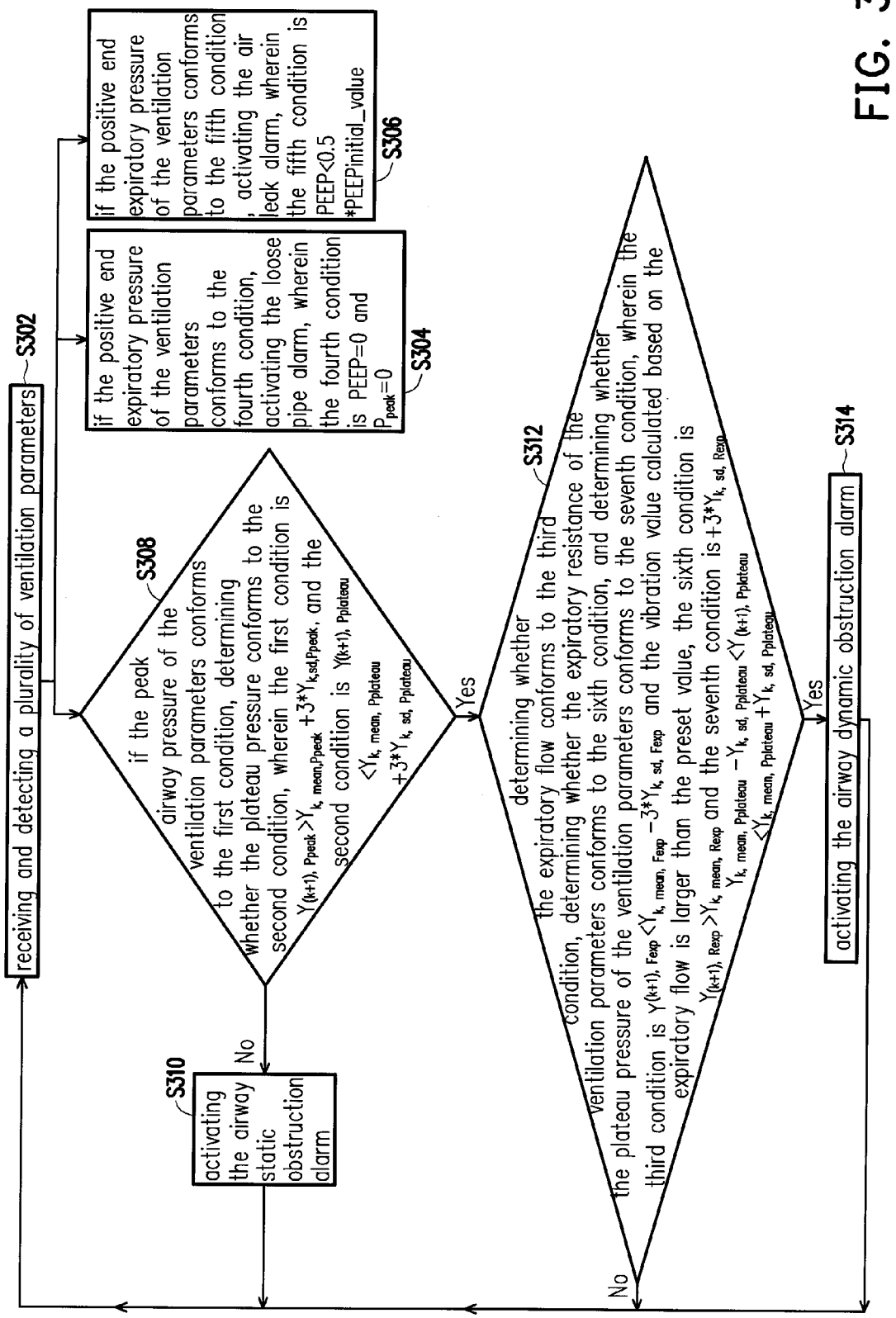
FIG. 3 is a flowchart illustrating an alarming method for a ventilator according to an embodiment of the invention.

FIG. 3 is a flowchart illustrating an alarming method for a ventilator according to an embodiment of the invention. With reference to FIG. 1 and FIG. 3, in Step S302, the control unit 120 receives the ventilation parameters from the ventilator 100 and detects the ventilation parameters obtained from the ventilator 100, thereby determining whether the ventilation parameters conform to one or a plurality of conditions. As shown in Step S304, if the positive end expiratory pressure PEEP of the ventilation parameters conforms to a fourth condition, the control unit 120 activates a loose pipe alarm through the monitoring apparatus 140, wherein the fourth condition is: PEEP=0 and Ppeak=0, and PEEP indicates the positive end expiratory pressure and Ppeak indicates the peak airway pressure. Moreover, as shown in Step S306, if the positive end expiratory pressure PEEP of the ventilation parameters conforms to a fifth condition, the control unit 120 activates an air leak alarm through the monitoring apparatus 140, wherein the fifth condition is: PEEP<0.5*$\text{PEEP}_{initial\_value}$, and $\text{PEEP}_{initial\_value}$ indicates an initial setting value of the positive end expiratory pressure PEEP. Accordingly, when a breathing pipe has a large air leak, the positive end expiratory pressure PEEP drops to 0. Therefore, by determining whether the positive end expiratory pressure PEEP conforms to the fourth condition (i.e. PEEP=0 and Ppeak=0), this embodiment activates the loose pipe alarm instantly to notify the medical staff of the situation. In addition, when the breathing pipe has a small air leak, a final value of the positive end expiratory pressure PEEP becomes smaller than the initial setting value. Thus, by determining whether the positive end expiratory pressure PEEP conforms to the fifth condition, this embodiment activates the air leak alarm instantly to notify the medical staff to adjust the breathing pipe.

In addition, as shown in Step S308, if the peak airway pressure Ppeak of the ventilation parameters conforms to the first condition (i.e. $Y_{(k+1), Ppeak} > Y_{k, mean, Ppeak} + 3 * Y_{k, sd, Ppeak}$), the control unit 120 further determines whether the plateau pressure Pplateau conforms to the second condition (i.e. $Y_{(k+1), Pplateau} < Y_{k, mean, Pplateau} + 3 * Y_{k, sd, Pplateau}$). If the plateau pressure Pplateau does not conform to the second condition, then as shown in Step S310, the control unit 120 activates the airway static obstruction alarm through the monitoring apparatus 140.

In this embodiment, if the plateau pressure Pplateau conforms to the second condition, then as shown in Step S312, the control unit 120 further determines whether the expiratory flow Fexp conforms to the third condition, determines whether an expiratory resistance Rexp of the ventilation parameters conforms to a sixth condition, and determines whether the plateau pressure Pplateau of the ventilation parameters conforms to a seventh condition. The third condition is $Y_{(k+1), Fexp} < Y_{k, mean, Fexp} - 3 * Y_{k, sd, Fexp}$, and the vibration value Vib calculated based on the expiratory flow Fexp is larger than the preset value; the sixth condition is $Y_{(k+1), Rexp} > Y_{k, mean, Rexp} + 3 * Y_{k, sd, Rexp}$; and the seventh condition is $Y_{k, mean, Pplateau} - Y_{k, sd, Pplateau} Y_{(k+1), Pplateau} < Y_{k, mean, Pplateau} + Y_{k, sd, Pplateau}$. $Y_{(k+1), Fexp}$ indicates the expiratory flow Fexp of the k+1$^{th}$ sample, and $Y_{k, mean, Fexp}$ and $Y_{k, sd, Fexp}$ respectively indicate the moving average and the standard deviation of the expiratory flow Fexp obtained based on the k$^{th}$ sample. The method of obtaining the vibration value Vib is the same as the above embodiment, wherein $Y_{(k+1), Pplateau}$ indicates the plateau pressure Pplateau of the k+1$^{th}$ sample, and $Y_{k,\ mean,\ Pplateau}$ and $Y_{k,\ sd,\ Pplateau}$ respectively indicate the moving average and the standard deviation of the plateau pressure Pplateau obtained based on the k$^{th}$ sample.

If this ventilation parameter conforms to the third condition, the sixth condition, and the seventh condition, i.e. the peak airway pressure Ppeak, the plateau pressure Pplateau, the expiratory flow Fexp, and the expiratory resistance Rexp of this ventilation parameter simultaneously conform to the first condition, the second condition, the third condition, the sixth condition, and the seventh condition, then as shown in Step S314, the control unit 120 activates the airway dynamic obstruction alarm through the monitoring apparatus 140. That is to say, when a diameter of the airway is narrowed due to the sputum, the peak airway pressure Ppeak and the expiratory resistance Rexp gradually increase, the plateau pressure Pplateau remains substantially unchanged, the expiratory flow Fexp gradually decreases, and the vibration value calculated based on the expiratory flow Fexp becomes larger than the preset value. Thus, by determining the above conditions, this embodiment issues the suctioning alarm instantly to notify the medical staff of the airway dynamic obstruction.

If the ventilation parameter does not conform to the first condition, the second condition, the third condition, the sixth condition, and the seventh condition simultaneously, then as shown in Step S302, the control unit 120 continues to detect the next ventilation parameter obtained by the ventilator 100 to determine whether the next ventilation parameter is abnormal.

When the patient has an abnormal physiological condition (e.g. sputum or asthma) or the pipe of the ventilator malfunctions (e.g. loose pipe or air leak), because the ventilation parameter of the patient exceeds the normal value range, the control unit 120 issues the corresponding alarm based on the result of determination through the monitoring apparatus 140 to notify the medical staff immediately.

It should be noted that, although FIG. 3 illustrates determining the fourth condition (i.e. Step S304) and the fifth condition (i.e. Step S306) first, Steps S308, S312, and S314 may be performed first according to other embodiments of the invention. The invention is not intended to limit the sequence in which the steps of FIG. 3 are performed.

Figure 4:
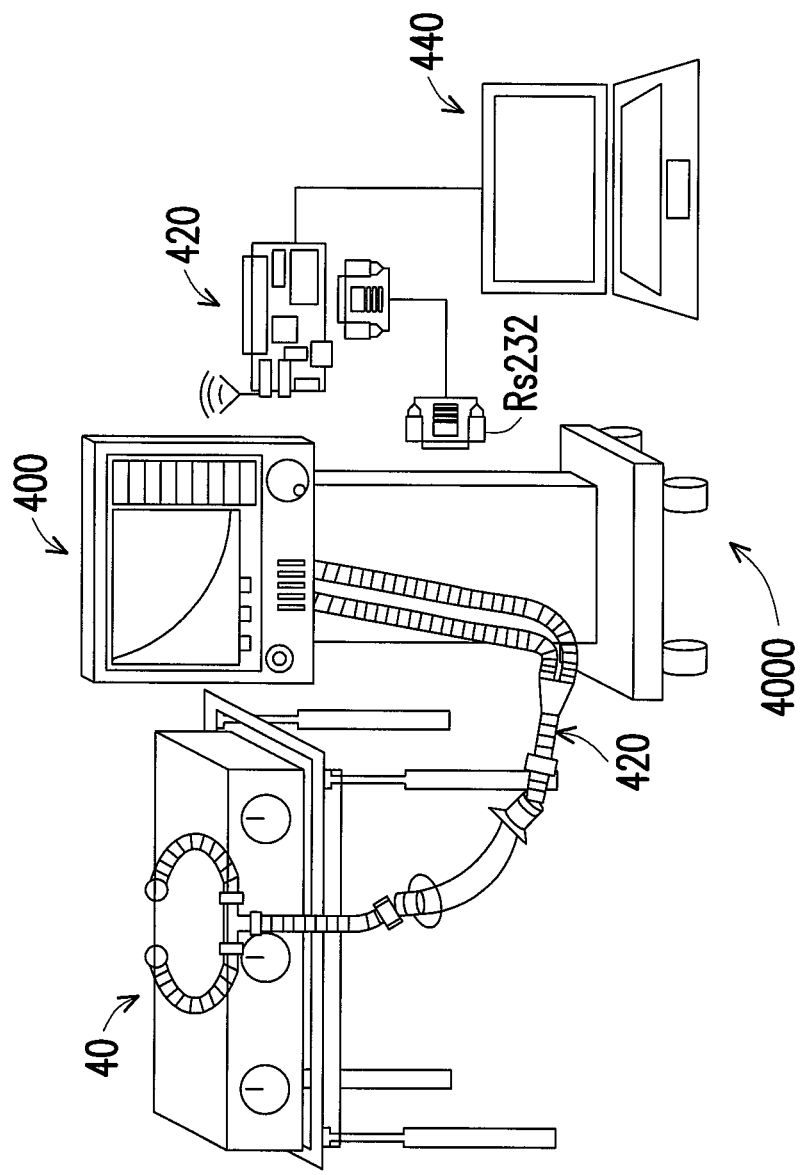
FIG. 4 is a schematic diagram illustrating a ventilator alarm system according to an embodiment of the invention.

To explain how to obtain the first to the seventh conditions in this embodiment, another embodiment is given below to illustrate an experimental method for constructing the ventilator alarm system and an experimental result thereof. FIG. 4 is a schematic diagram illustrating the ventilator alarm system according to an embodiment of the invention. With reference to FIG. 4, a ventilator alarm system 4000 includes a simulated lung 40, a ventilator 400, a control unit 420, and a monitoring apparatus 440. In this embodiment, the simulated lung 40 and the ventilator 400 are used to simulate various breathing states of the patient, and the control unit 420 is used to analyze the variation of the ventilation parameter corresponding to each breathing state, so as to obtain the first to the seventh conditions as bases for determining whether the patient has an abnormal breathing state or the pipe of the ventilator 400 malfunctions. Then, the corresponding alarm is issued through the monitoring apparatus 440 according to the result of determination.

To be more specific, the ventilator 400 used in this embodiment is Hamilton Galileo (G5) produced by Hamilton Medical AG, Bonaduz Switzerland. The ventilator 400 is connected with an artificial airway 402 connected to the simulated lung 40 (Training and Test Lungs (TTL), Michigan Instruments) that simulates the breathing state of the patient and is connected with the ventilator pipe and a flow sensor for detecting the ventilation parameters. Moreover, the ventilator alarm system 4000 further includes an artificial sputum device, which is connected with the ventilator 400 and provides mucus simulants, so as to simulate the situation when the patient has sputum. In addition, the control unit 420 may retrieve various ventilation parameters of the ventilator 400 through a Rs232 communication interface and determine whether the ventilation parameters conform to one or a plurality of conditions for issuing alarms, and further use a WiFi module or a TCP/IP module for wired or wireless transmission so as to transmit the ventilation parameters to the monitoring apparatus 440 and enable the monitoring apparatus 440 to issue a series of alarms correspondingly to notify the medical staff. Variations of the ventilation parameters detected by the control unit 420 in different breathing states are explained below.

Figure 5A:
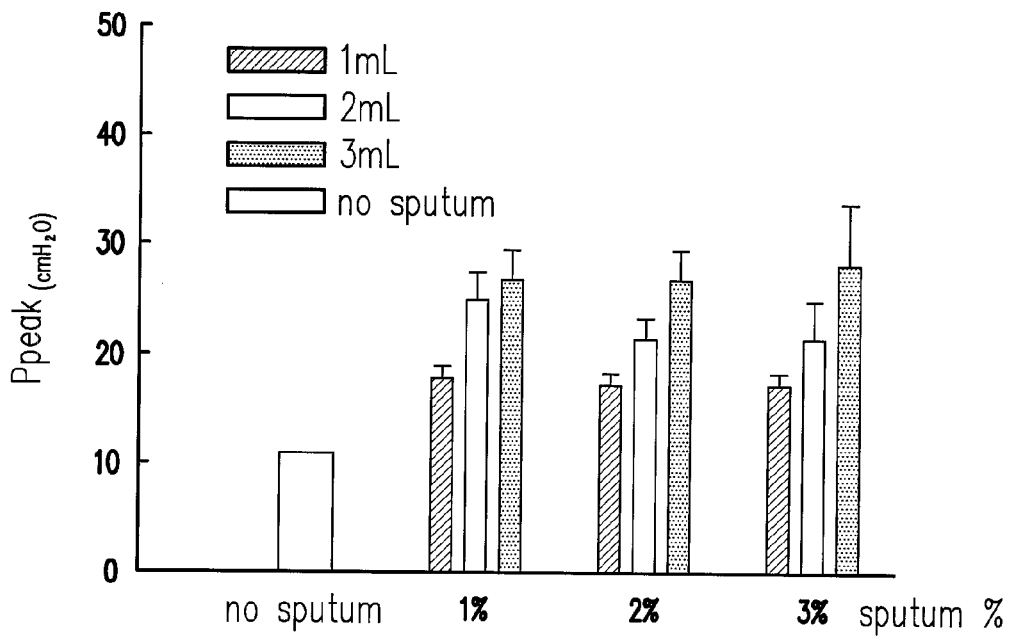
FIG. 5A and FIG. 5B respectively illustrate a variation of a ventilation parameter provided by a simulated lung at different sputum concentrations and different sputum volumes.
Figure 5B:
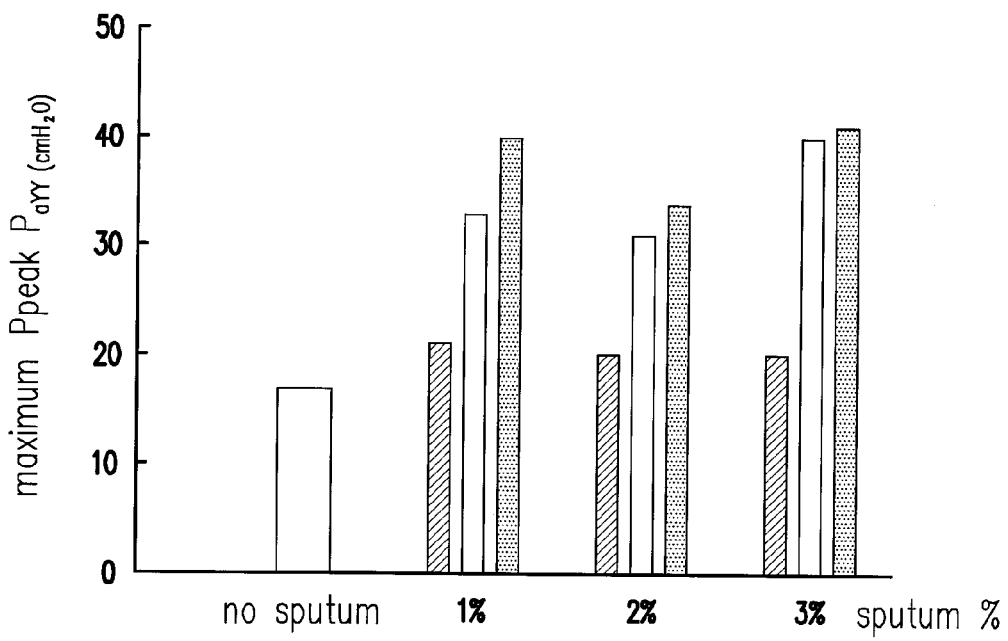

FIG. 5A and FIG. 5B respectively illustrate the variations of the ventilation parameters provided by the simulated lung 40 at different sputum concentrations and different sputum volumes, wherein a compliance (referred to as "C" hereinafter) of the simulated lung 40 is 0.05 cmH$_2$O/L, and the airway resistance is 5 cmH$_2$O/L/sec. Moreover, the horizontal axes of FIG. 5A and FIG. 5B respectively correspond to different sputum concentrations. The vertical axis of FIG. 5A corresponds to the peak airway pressure Ppeak (cmH$_2$O), and the vertical axis of FIG. 5B corresponds to a maximum peak airway pressure (cmH$_2$O). The bars in FIG. 5A and FIG. 5B respectively correspond to different sputum volumes (mL). With reference to FIG. 5, the peak airway pressure Ppeak and the maximum peak airway pressure Ppeak increase as the sputum volumes and the sputum concentrations increase. The above shows that the simulated lung 40 used for constructing the ventilator alarm system 4000 matches the situation where the patient produces sputum when breathing.

Figure 6:
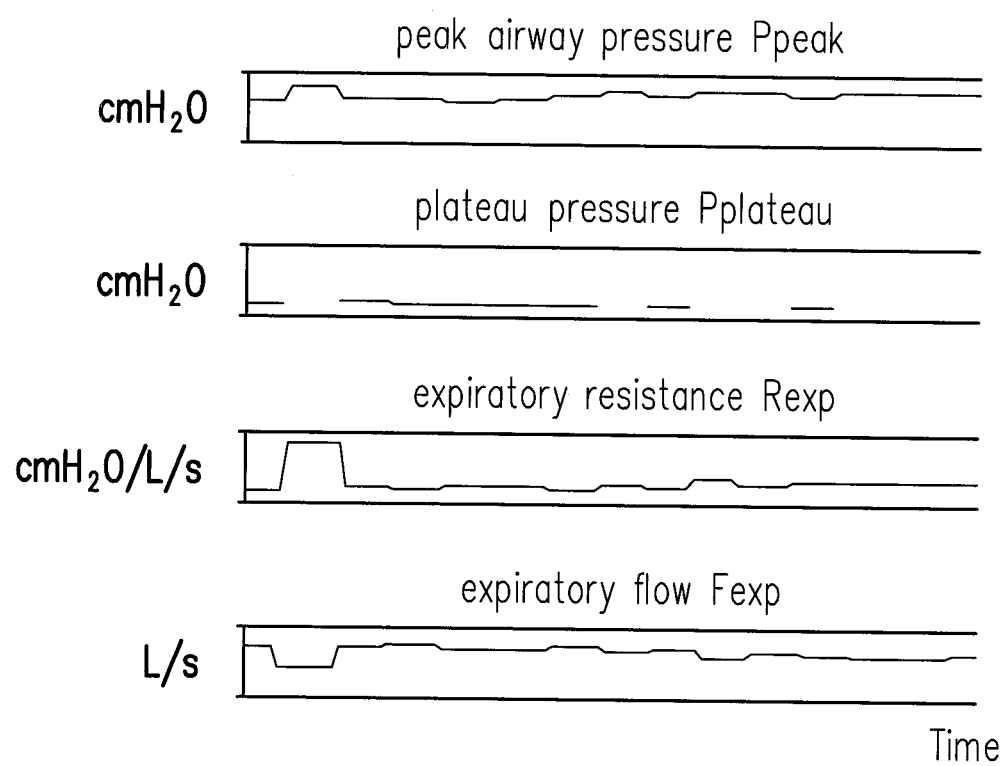
FIG. 6 illustrates variations of a variety of ventilation parameters with time when simulated sputum is generated.

FIG. 6 illustrates variations of various ventilation parameters (i.e. peak airway pressure Ppeak, expiratory resistance Rexp, plateau pressure Pplateau, and expiratory flow Fexp) with time when simulated sputum is generated, wherein the compliance of the simulated lung 40 is 0.02 cmH$_2$O/L, the airway resistance is 5 cmH$_2$O/L/sec, and the simulated sputum volume is 2.5 cc. It is known from FIG. 6 that, when the ventilator alarm system 4000 provides artificial sputum, the peak airway pressure Ppeak and the expiratory resistance Rexp gradually increase while the expiratory flow Fexp gradually decreases, and the plateau pressure Pplateau remains substantially unchanged.

Figure 7A:
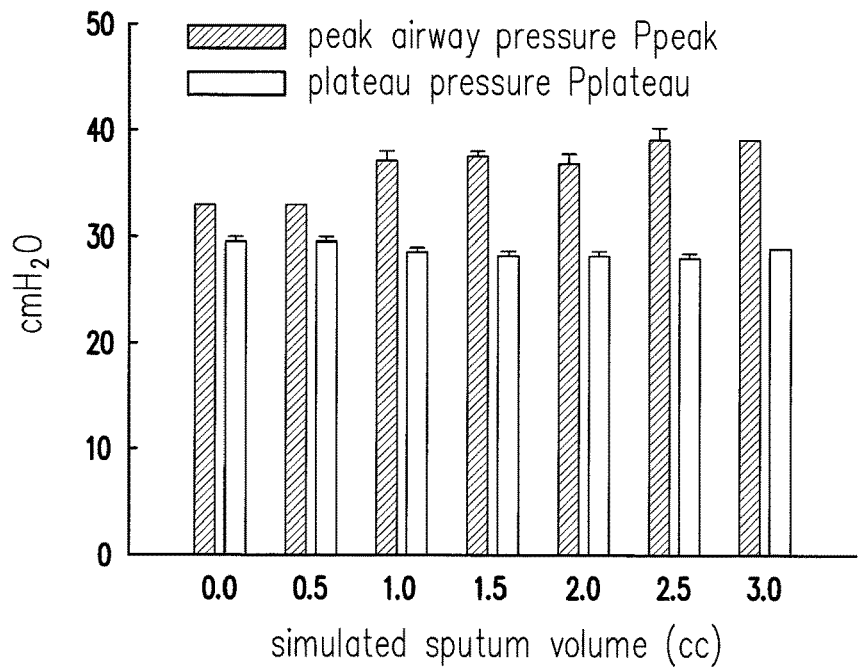
FIG. 7A illustrates averages of a peak airway pressure and a plateau pressure when different sputum volumes are injected.
Figure 7B:
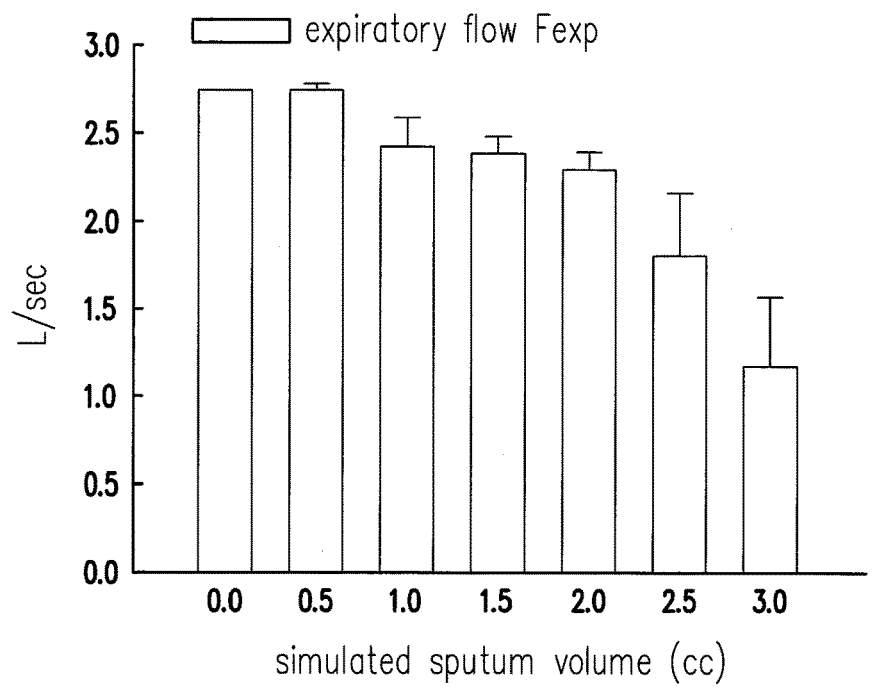
FIG. 7B illustrates expiratory flows when different sputum volumes are injected.

FIG. 7A illustrates averages of the peak airway pressure Ppeak and the plateau pressure Pplateau when different sputum volumes are injected. FIG. 7B illustrates the corresponding expiratory flows Fexp when different sputum volumes are injected. It is known from FIG. 7A and FIG. 7B that, as the sputum volume increases, the peak airway pressure Ppeak gradually increases, the plateau pressure Pplateau remains substantially unchanged, and the expiratory flow Fexp gradually decreases.

Figure 8:
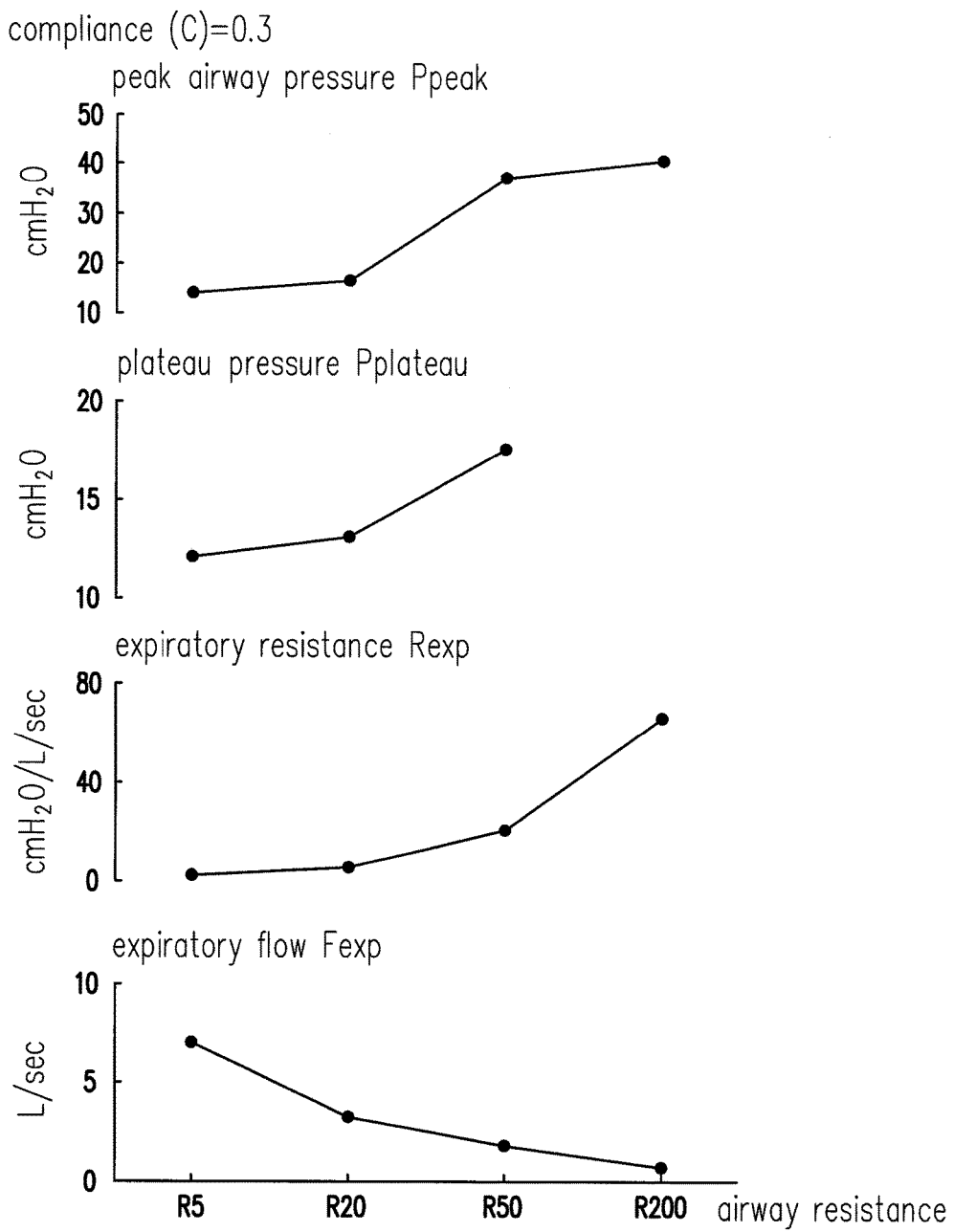
FIG. 8 illustrates variations of a variety of ventilation parameters at different airway resistances when a compliance of a simulated lung is fixed.

FIG. 8 illustrates variations of various ventilation parameters (i.e. peak airway pressure Ppeak, expiratory resistance Rexp, plateau pressure Pplateau, and expiratory flow Fexp) at different airway resistances when the compliance of the simulated lung 40 is fixed at 0.3 cmH$_2$O/L. This experiment is for simulating the breathing state of the patient who has asthma, i.e. simulating the situation where the patient has airway static obstruction. It is known from FIG. 8 that, as the airway resistance increases, the peak airway pressure Ppeak, the plateau pressure Pplateau, and the expiratory resistance Rexp gradually increase but the expiratory flow Fexp gradually decreases.

Figure 9:
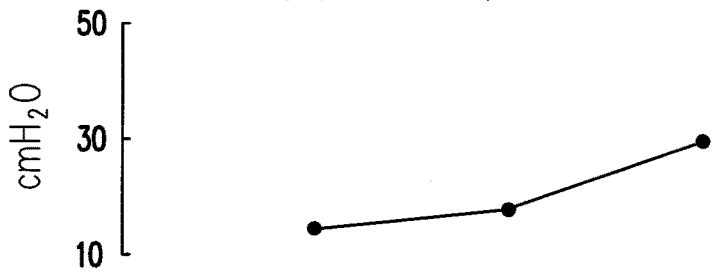
FIG. 9 illustrates variations of a variety of ventilation parameters at different compliances of a simulated lung when an airway resistance is fixed.
Figure 9:
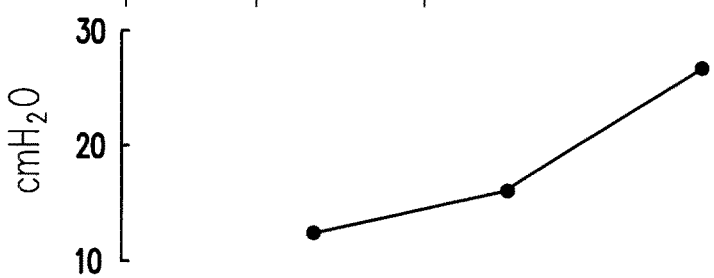
Figure 9:
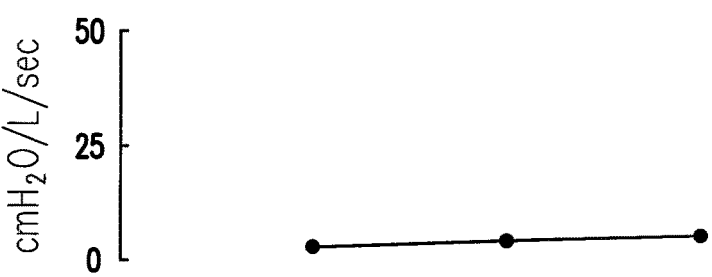
Figure 9:
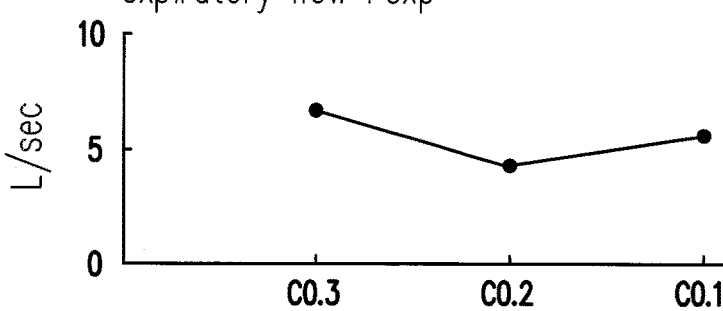

FIG. 9 illustrates variations of various ventilation parameters (i.e. peak airway pressure Ppeak, expiratory resistance Rexp, plateau pressure Pplateau, and expiratory flow Fexp) at different compliances of the simulated lung 40 when the airway resistance is fixed at 0.5 cmH$_2$O/L/sec. This experiment is for simulating the breathing state of the patient who has pneumonia alveolar damage, i.e. simulating the situation where the patient has airway dynamic obstruction. It is known from FIG. 9 that, as the compliance increases, the peak airway pressure Ppeak and the plateau pressure Pplateau gradually increase, the expiratory resistance Rexp remains substantially unchanged, and the expiratory flow Fexp does not show a relative variation with respect to the airway resistance. In addition, it is known from FIG. 8 and FIG. 9 that, when the patient has airway static obstruction or airway dynamic obstruction, information of different ventilation parameters is obtained from the patient.

Figure 10A:
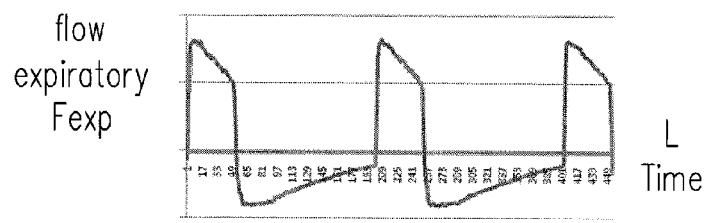
FIG. 10A and FIG. 10B respectively illustrate variations of expiratory flows with and without sputum injection.
Figure 10B:
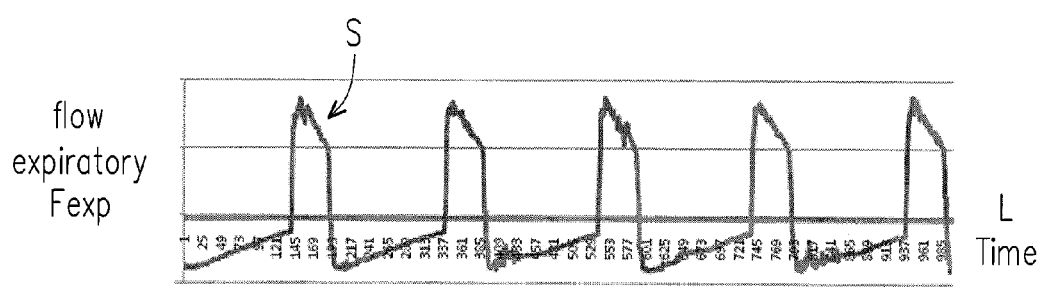

FIG. 10A and FIG. 10B respectively illustrate variations of the expiratory flow Fexp with and without sputum injection, wherein the compliance of the simulated lung 40 is 0.05 cmH$_2$O/L and the airway resistance is 5 cmH$_2$O/L/sec. Moreover, in FIG. 10A and FIG. 10B, a signal above a reference line L indicates an inspiratory flow of simulated inspiration, and a signal below the reference line L indicates the expiratory flow Fexp of simulated expiration. A comparison between FIG. 10A (without sputum injection) and FIG. 10B (with sputum injection) shows that, when sputum is injected, a saw-tooth variation is observed in the detected expiratory flow Fexp. Furthermore, it is known from FIG. 10A (without sputum injection) that, when no sputum is injected, the vibration value Vib calculated based on the expiratory flow Fexp is smaller than the preset value. Thus, the above proves that, when the control unit 420 detects the vibration value Vib of the expiratory flow Fexp is larger than the preset value, sputum is generated when the patient breathes. Accordingly, the alarm is activated through the monitoring apparatus 440 to notify the medical staff that suctioning is required.

According to the experimental method and the experimental result of FIG. 5A to FIG. 10B, it is known that the corresponding alarm needs to be activated when the ventilation parameters conform to the first to the seventh conditions (as illustrated in FIG. 3). Further, the sensitivity, specificity, and P-value of the alarms issued by the ventilator alarm system 4000 of this embodiment and the corresponding alarms are specified in the following Table 1. Thus, this embodiment shows that use of the ventilator alarm system 4000 in different simulated clinical situations improves the safety of the patient.

TABLE 1

| | alarm type | sensitivity | specificity | P-value |
|---|---|---|---|---|
| high pressure | airway static obstruction alarm | 80% | 100% | 0.04 |
| | airway dynamic obstruction alarm | 80% | 100% | 0.04 |
| low pressure | air leak alarm | 100% | 100% | 0.008 |
| | loose pipe alarm | 100% | 100% | 0.008 |

To conclude the above, in the ventilator alarming method and the ventilator alarm system of the embodiments, the control unit determines whether the ventilation parameters that the ventilator receives from the patient conform to one or a plurality of conditions. The monitoring apparatus issues the airway dynamic obstruction alarm if the peak airway pressure Ppeak gradually increases, the plateau pressure Pplateau remains substantially unchanged, the expiratory flow Fexp substantially decreases, and the vibration value of the expiratory flow Fexp conforms to the preset equation. The monitoring apparatus issues the airway static obstruction alarm if the peak airway pressure Ppeak and the plateau pressure Pplateau both increase gradually. In addition, if the positive end expiratory pressure PEEP drops down to 0 and the peak airway pressure Ppeak is equal to 0, the monitoring apparatus issues the loose pipe alarm. If the positive end expiratory pressure is smaller than the initial setting value, the monitoring apparatus issues the air leak alarm. Accordingly, the medical staff can perform treatment or management immediately based on the alarms of the various conditions.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. An alarming method for a ventilator, the alarming method comprising:
   receiving and detecting a plurality of ventilation parameters;
   determining whether a plateau pressure conforms to a second condition if a peak airway pressure of the ventilation parameters conforms to a first condition, wherein the first condition is $Y_{(k+1), Ppeak} > Y_{k, mean, Ppeak} + 3*Y_{k, sd, Ppeak}$ and the second condition is $Y_{(k+1), Pplateau} < Y_{k, mean, Pplateau} + 3*Y_{k, sd, Pplateau}$; wherein k is a positive integer which indicates a $k^{th}$ sample, $Y_{(k+1), Ppeak}$ indicates the peak airway pressure of a $k+1^{th}$ sample, $Y_{k, mean, Ppeak}$ and $Y_{k, sd, Ppeak}$ respectively indicate a moving average and a standard deviation of the peak airway pressure obtained based on the $k^{th}$ sample, $Y_{(k+1), Pplateau}$ indicates the plateau pressure of the $k+1^{th}$ sample, and $Y_{k, mean, Pplateau}$ and $Y_{k, sd, Pplateau}$ respectively indicate a moving average and a standard deviation of the plateau pressure obtained based on the $k^{th}$ sample;
   activating an airway static obstruction alarm if the plateau pressure does not conform to the second condition; and
   activating an airway dynamic obstruction alarm if the plateau pressure conforms to the second condition and an expiratory flow of the ventilation parameters conforms to a third condition.

2. The alarming method according to claim 1, wherein the third condition is $Y_{(k+1), Fexp} < Y_{k, mean, Fexp} - 3*Y_{k, sd, Fexp}$; wherein $Y_{(k+1), Fexp}$ indicates the expiratory flow of the $k+1^{th}$ sample, and $Y_{k, mean, Fexp}$ and $Y_{k, sd, Fexp}$ respectively indicate a moving average and a standard deviation of the expiratory flow obtained based on the $k^{th}$ sample.

3. The alarming method according to claim 1, wherein the third condition comprises that a vibration value calculated based on the expiratory flow is larger than a preset value, wherein a step of calculating the vibration value comprises:
   performing a segmentation calculation on the expiratory flow and performing a curve fitting calculation to obtain a flow trend of the expiratory flow; and
   calculating a difference equation based on a result of performing the segmentation calculation on the expiratory flow and the flow trend, and calculating the vibration value by the difference equation.

4. The alarming method according to claim 1, further comprising:
activating a loose pipe alarm if a positive end expiratory pressure of the ventilation parameters conforms to a fourth condition, wherein the fourth condition is PEEP=0 and Ppeak=0, and PEEP indicates the positive end expiratory pressure and Ppeak indicates the peak airway pressure.

5. The alarming method according to claim 4, further comprising:
activating an air leak alarm if the positive end expiratory pressure of the ventilation parameters conforms to a fifth condition, wherein the fifth condition is PEEP<0.5*$PEEP_{initial\_value}$, and $PEEP_{initial\_value}$ is an initial setting value of PEEP.

6. The alarming method according to claim 1, wherein the ventilation parameters comprise the peak airway pressure, the positive end expiratory pressure, an expiratory tidal volume, an inspiratory tidal volume, a percentage of inhaled oxygen, a respiratory rate, an airway resistance, the expiratory flow, and expiratory flow waveform information thereof.

7. The alarming method according to claim 1, wherein the step of detecting the ventilation parameters comprises:
respectively sampling five of each of the ventilation parameters for calculating the moving averages and the standard deviations respectively corresponding to the ventilation parameters, wherein sampling time is 0.5 second each time.

8. The alarming method according to claim 1, further comprising:
activating the airway dynamic obstruction alarm if the ventilation parameters conform to the first condition, the second condition, and the third condition, and an expiratory resistance of the ventilation parameters conforms to a sixth condition, wherein the sixth condition is $Y_{(k+1),\ Rexp} > Y_{k,\ mean,\ Rexp} + 3*Y_{k,\ sd,\ Rexp}$, wherein $Y_{(k+1),\ Rexp}$ indicates the expiratory resistance of the $k+1^{th}$ sample, and $Y_{k,\ mean,\ Rexp}$ and $Y_{k,\ sd,\ Rexp}$ respectively indicate a moving average and a standard deviation of the expiratory resistance obtained based on the $k^{th}$ sample.

9. The alarming method according to claim 8, further comprising:
activating the airway dynamic obstruction alarm if the ventilation parameters conform to the first condition, the second condition, the third condition, and the sixth condition, and the plateau pressure of the ventilation parameters conforms to a seventh condition, wherein the seventh condition is $Y_{k,\ mean,\ Pplateau} - Y_{k,\ sd,\ Pplateau} < Y_{(k+1),\ Pplateau} < Y_{k,\ mean,\ Pplateau} + Y_{k,\ sd,\ Pplateau}$, wherein $Y_{(k+1),\ Pplateau}$ indicates the plateau pressure of the $k+1^{th}$ sample, and $Y_{k,\ mean,\ Pplateau}$ and $Y_{k,\ sd,\ Pplateau}$ respectively indicate the moving average and the standard deviation of the plateau pressure obtained based on the $k^{th}$ sample.

10. The alarming method according to claim 1, wherein the ventilation parameters are provided by a ventilator and transmitted to a control unit for analysis through a network.

11. A ventilator alarm system, comprising:
a ventilator configured to receive a plurality of ventilation parameters from a patient;
a control unit configured to receive the ventilation parameters from the ventilator, detect the ventilation parameters, and determine whether the ventilation parameters conform to a plurality of conditions; and
a monitoring apparatus configured to display information corresponding to the ventilation parameters and issue a plurality of alarms, wherein
if the control unit determines that a peak airway pressure of the ventilation parameters conforms to a first condition, the control unit determines whether a plateau pressure conforms to a second condition, wherein the first condition is $Y_{(k+1),\ Ppeak} > Y_{k,\ mean,Ppeak} + 3*Y_{k,sd,Ppeak}$ mean, and the second condition is $Y_{(k+1),\ Pplateau} < Y_{k,\ mean,\ Pplateau} + 3*Y_{k,\ sd,\ Pplateau}$; wherein k is a positive integer which indicates a $k^{th}$ sample, $Y_{(k+1),\ Ppeak}$ indicates the peak airway pressure of a $k+1^{th}$ sample, $Y_{k,\ mean,Ppeak}$ and $Y_{k,\ sd,\ Ppeak}$ respectively indicate a moving average and a standard deviation of the peak airway pressure obtained based on the $k^{th}$ sample, $Y_{(k+1),\ Pplateau}$ indicates the plateau pressure of the $k+1^{th}$ sample, and $Y_{k,\ mean,\ Pplateau}$ and $Y_{k,\ sd,\ Pplateau}$ respectively indicate a moving average and a standard deviation of the plateau pressure obtained based on the $k^{th}$ sample;
if the control unit determines that the plateau pressure does not conform to the second condition, the monitoring apparatus activates an airway static obstruction alarm; and
if the control unit determines that the plateau pressure conforms to the second condition and an expiratory flow of the ventilation parameters conforms to a third condition, the monitoring apparatus activates an airway dynamic obstruction alarm.

12. The ventilator alarm system according to claim 11, wherein the third condition is $Y_{(k+1),\ Fexp} < Y_{k,\ mean,\ Fexp} - 3*Y_{k,\ sd,\ Fexp}$, wherein $Y_{(k+1),\ Fexp}$ indicates the expiratory flow of the $k+1^{th}$ sample, and $Y_{k,\ mean,\ Fexp}$ and $Y_{k,\ sd,\ Fexp}$ respectively indicate a moving average and a standard deviation of the expiratory flow obtained based on the $k^{th}$ sample.

13. The ventilator alarm system according to claim 11, wherein the third condition comprises that a vibration value calculated by the control unit based on the expiratory flow is larger than a preset value, wherein a step by which the control unit calculates the vibration value comprises:
performing a segmentation calculation on the expiratory flow and performing a curve fitting calculation to obtain a flow trend of the expiratory flow; and
calculating a difference equation based on a result of performing the segmentation calculation on the expiratory flow and the flow trend, and calculating the vibration value by the difference equation.

14. The ventilator alarm system according to claim 11, further comprising:
the monitoring apparatus activates a loose pipe alarm if the control unit determines that a positive end expiratory pressure of the ventilation parameters conforms to a fourth condition, wherein the fourth condition is PEEP=0 and Ppeak=0, and PEEP indicates the positive end expiratory pressure and Ppeak indicates the peak airway pressure.

15. The ventilator alarm system according to claim 14, further comprising:
the monitoring apparatus activates an air leak alarm if the control unit determines that the positive end expiratory pressure of the ventilation parameters conforms to a fifth condition, wherein the fifth condition is PEEP<0.5*$PEEP_{initial\_value}$, and $PEEP_{initial\_value}$ is an initial setting value of PEEP.

16. The ventilator alarm system according to claim 11, wherein the ventilation parameters comprise the peak airway pressure, the positive end expiratory pressure, an expiratory tidal volume, an inspiratory tidal volume, a percentage of inhaled oxygen, a respiratory rate, an airway resistance, the expiratory flow, and expiratory flow waveform information thereof.

17. The ventilator alarm system according to claim 11, wherein the control unit respectively samples five of each of the ventilation parameters for calculating the moving averages and the standard deviations respectively corresponding to the ventilation parameters, wherein sampling time is 0.5 second each time.

18. The ventilator alarm system according to claim 11, wherein the monitoring apparatus activates the airway dynamic obstruction alarm if the control unit determines that the ventilation parameters conform to the first condition, the second condition, and the third condition, and determines that an expiratory resistance of the ventilation parameters conforms to a sixth condition, wherein the sixth condition is $Y_{(k+1), Rexp} > Y_{k, mean, Rexp} + 3*Y_{k, sd, Rexp}$, wherein $Y_{(k+1), Rexp}$ indicates the expiratory resistance of the $k+1^{th}$ sample, and $Y_{k, mean, Rexp}$ and $Y_{k, sd, Rexp}$ respectively indicate a moving average and a standard deviation of the expiratory resistance obtained based on the $k^{th}$ sample.

19. The ventilator alarm system according to claim 18, further comprising:
the monitoring apparatus activates the airway dynamic obstruction alarm if the control unit determines that the ventilation parameters conform to the first condition, the second condition, the third condition, and the sixth condition, and the plateau pressure of the ventilation parameters conforms to a seventh condition, wherein the seventh condition is $Y_{k, mean, Pplateau} - Y_{k, sd, Pplateau} < Y_{(k+1), Pplateau} < Y_{k, mean, Pplateau} + Y_{k, sd, Pplateau}$, wherein $Y_{(k+1), Pplateau}$ indicates the plateau pressure of the $k+1^{th}$ sample, and $Y_{k, mean, Pplateau}$ and $Y_{k, sd, Pplateau}$ respectively indicate the moving average and the standard deviation of the plateau pressure obtained based on the $k^{th}$ sample.

20. The ventilator alarm system according to claim 11, wherein the ventilator transmits the ventilation parameters to the control unit for analysis through a network.

21. An alarming method for a ventilator, the alarming method comprising:
receiving and detecting a plurality of ventilation parameters;
determining whether a plateau pressure conforms to a second condition if a peak airway pressure of the ventilation parameters conforms to a first condition, wherein the first condition is $Y_{(k+1), Ppeak} > Y_{k, mean, Ppeak} + 3*Y_{k, sd, Ppeak}$ and the second condition is $Y_{(k+1), Pplateau} < Y_{k, mean, Pplateau} + 3*Y_{k, sd, Pplateau}$; wherein k is a positive integer which indicates a $k^{th}$ sample, $Y_{(k+1), Ppeak}$ indicates the peak airway pressure of a $k+1^{th}$ sample, $Y_{k, mean, Ppeak}$ and $Y_{k, sd, Ppeak}$ respectively indicate a moving average and a standard deviation of the peak airway pressure obtained based on the $k^{th}$ sample, $Y_{(k+1), Pplateau}$ indicates the plateau pressure of the $k+1^{th}$ sample, and $Y_{k, mean, Pplateau}$ and $Y_{k, sd, Pplateau}$ respectively indicate a moving average and a standard deviation of the plateau pressure obtained based on the $k^{th}$ sample;
activating an airway static obstruction alarm if the plateau pressure does not conform to the second condition;
activating an airway dynamic obstruction alarm if the plateau pressure conforms to the second condition and an expiratory flow of the ventilation parameters conforms to a third condition, wherein the third condition comprises that a vibration value calculated based on the expiratory flow is larger than a preset value, wherein a step of calculating the vibration value comprises:
performing a segmentation calculation on the expiratory flow and performing a curve fitting calculation to obtain a flow trend of the expiratory flow; and
calculating a difference equation based on a result of performing the segmentation calculation on the expiratory flow and the flow trend, and calculating the vibration value by the difference equation;
activating a loose pipe alarm if a positive end expiratory pressure of the ventilation parameters conforms to a fourth condition, wherein the fourth condition is PEEP=0 and Ppeak=0, and PEEP indicates the positive end expiratory pressure and Ppeak indicates the peak airway pressure; and
activating an air leak alarm if the positive end expiratory pressure of the ventilation parameters conforms to a fifth condition, wherein the fifth condition is PEEP<0.5*$PEEP_{initial\_value}$, and $PEEP_{initial\_value}$ is an initial setting value of PEEP.

22. A ventilator alarm system, comprising:
a ventilator configured to receive a plurality of ventilation parameters from a patient;
a control unit configured to receive the ventilation parameters from the ventilator, detect the ventilation parameters, and determine whether the ventilation parameters conform to a plurality of conditions; and
a monitoring apparatus configured to display information corresponding to the ventilation parameters and issue a plurality of alarms, wherein
if the control unit determines that a peak airway pressure of the ventilation parameters conforms to a first condition, the control unit determines whether a plateau pressure conforms to a second condition, wherein the first condition is $Y_{(k+1), Ppeak} > Y_{k, mean, Ppeak} + 3*Y_{k, sd, Ppeak}$ and the second condition is $Y_{(k+1), Pplateau} < Y_{k, mean, Pplateau} + 3*Y_{k, sd, Pplateau}$; wherein k is a positive integer which indicates a $k^{th}$ sample, $Y_{(k+1), Ppeak}$ indicates the peak airway pressure of a $k+1^{th}$ sample, $Y_{k, mean, Ppeak}$ and $Y_{k, sd, Ppeak}$ respectively indicate a moving average and a standard deviation of the peak airway pressure obtained based on the $k^{th}$ sample, $Y_{(k+1), Pplateau}$ indicates the plateau pressure of the $k+1^{th}$ sample, and $Y_{k, mean, Pplateau}$ and $Y_{k, sd, Pplateau}$ respectively indicate a moving average and a standard deviation of the plateau pressure obtained based on the $k^{th}$ sample;
if the control unit determines that the plateau pressure does not conform to the second condition, the monitoring apparatus activates an airway static obstruction alarm;
if the control unit determines that the plateau pressure conforms to the second condition and an expiratory flow of the ventilation parameters conforms to a third condition, the monitoring apparatus activates an airway dynamic obstruction alarm, wherein the third condition comprises that a vibration value calculated by the control unit based on the expiratory flow is larger than a preset value, wherein a step by which the control unit calculates the vibration value comprises:
performing a segmentation calculation on the expiratory flow and performing a curve fitting calculation to obtain a flow trend of the expiratory flow; and calculating a difference equation based on a result of performing the segmentation calculation on the expiratory flow and the flow trend, and calculating the vibration value by the difference equation;

if the control unit determines that a positive end expiratory pressure of the ventilation parameters conforms to a fourth condition, the monitoring apparatus activates a loose pipe alarm, wherein the fourth condition is PEEP=0 and Ppeak=0, and PEEP indicates the positive end expiratory pressure and Ppeak indicates the peak airway pressure; and if the control unit determines that the positive end expiratory pressure of the ventilation parameters conforms to a fifth condition, the monitoring apparatus activates an air leak alarm, wherein the fifth condition is $PEEP<0.5*PEEP_{initial\_value}$, and $PEEP_{initial\_value}$ is an initial setting value of PEEP.

* * * * *